United States Patent [19]

Janssen et al.

[11] Patent Number: 4,940,827

[45] Date of Patent: Jul. 10, 1990

[54] CATALYST SYSTEM FOR OLEFIN DISPROPORTIONATION

[75] Inventors: Frank J. Janssen; Coenraad H. Wilms; Donald Reinalda; Hendrik W. Bruijn, all of Am Amsterdam, Netherlands

[73] Assignee: Shell Oil Company, Houston, Tex.

[21] Appl. No.: 437,146

[22] Filed: Nov. 16, 1989

Related U.S. Application Data

[62] Division of Ser. No. 272,590, Nov. 17, 1988, Pat. No. 4,916,102.

[30] Foreign Application Priority Data

Nov. 18, 1987 [GB] United Kingdom ................. 8726925

[51] Int. Cl.$^5$ ............................................... C07C 6/04
[52] U.S. Cl. ..................................... 585/646; 585/643
[58] Field of Search ......................... 585/646, 643, 644

[56] References Cited

U.S. PATENT DOCUMENTS

| | | | |
|---|---|---|---|
| 3,692,695 | 9/1972 | Suggitt et al. | 502/220 |
| 3,996,166 | 12/1976 | Banks et al. | 252/437 |
| 4,368,141 | 1/1983 | Kukes | 585/646 X |

FOREIGN PATENT DOCUMENTS

| | | |
|---|---|---|
| 62-8768 | 2/1987 | Japan . |
| 83043 | 4/1987 | Japan . |

OTHER PUBLICATIONS

*Journal of Catalysis,* vol. 33, pp. 83–90 (1974); vol. 70, pp. 364–374 (1981).
*Journal of Molecular Catalysis,* vol. 15, pp. 157–172 and 173–185 (1982).
*Bulletin of the Japan Petroleum Institute,* vol. 18(2), pp. 162–166 (1976).
*Bulletin of the Chemical Society of Japan,* vol. 50(4), pp. 998–1002 (1977).
*Chem Tech,* Feb. 1986, pp. 112–117.

*Primary Examiner*—Asok Pal

[57] ABSTRACT

1. A catalyst system for olefin disproportionation containing molybdenum oxide supported on alumina prepared by a process which comprises:
(a) comulling a gamma alumina providing agent with a sulfur-containing compound and/or a phosphorus-containing compound to produce a homogeneous mass,
(b) extruding the mass and dividing it into small particles,
(c) drying and calcining said particles at a temperature in the range of from about 400° C. to about 800° C.
(d) subjecting said particles to at least one additional step comprising: (1) impregnating said particles with a solution of molybdenum oxide(s), (2) drying and (3) calcining said impregnated particles at a temperature in the range of from about 400° C. to about 800° C.

21 Claims, No Drawings

CATALYST SYSTEM FOR OLEFIN DISPROPORTIONATION

This is a division of application Ser. No. 272,590 filed Nov. 17, 1988, now U.S. Pat. No. 4,916,102.

FIELD OF THE INVENTION

The invention relates to a catalyst system for olefin disproportionation and to a process using such catalyst systems More particularly the invention relates to an olefin disproportionation catalyst containing molybdenum oxide supported on an alumina carrier.

BACKGROUND OF THE INVENTION

Such a catalyst system is known from e.g. *J. Catalysis*, Vol. 33, p. 83–90 (1974); *J. Catalysis*, Vol. 70, p. 364–374 (1981); *J. Mol. catalysis*, Vol. 15, p. 157–172 and 173–185; *Bull. Jap. Petroleum Institute*, Vol. 18 (2) p. 162–166 (1976); *Bull. Chem. Soc. Japan*, Vol. 50 (4), p. 998–1002 (1977); and *Chemtech*, Feb. 1986, p. 112–117.

In these publications research efforts are described aiming at improved olefin disproportionation selectivity by pretreatment of $MoO_3/Al_2O_3$ catalyst systems. This pretreatment actually consisted of the insertion of large polarizable cations such as K, Cs, Rb and Tl or addition of other copromotors, e.g. cobalt oxide, into molybdenum oxides-alumina systems and/or calcination of the initially prepared impregnated alumina carrier at varying temperatures and under varying gas atmospheres.

Varying degrees of reduction with hydrogen gas at different reduction temperatures of molybdenum-alumina catalysts for the disproportionation of lower olefins, were tried to improve the disproportionation selectivity, such as that disclosed in Japanese Patent Publication No. 28768-1987 which discloses a process for the disproportion of olefins, in the presence of a catalyst prepared by reducing a molybdenum tri-oxide carrying solid composite, to such an extent that the amount of the oxygen atoms is between 2.9 and 2.2 gram atoms per gram atom of molybdenum.

On the other hand, more recent efforts to improve the selectivity of molybdenum-alumina catalysts were directed to activation by means of organo-metal derivatives, such as those disclosed in Japanese Patent Publication No. 83043-1987 and Russian Patent No. 1,264,973.

It will be appreciated that there is still a great current interest in molybdenum-alumina catalysts to be used in hydrocarbon chemistry, due to the wide range of reactions to which they can be applied, and that during the past several years extensive research efforts continued, however without providing any desired disproportionation catalyst system. Such a desired catalyst system has to meet the demands of modern industrial processes, one of which relates to disproportionation of more particularly higher olefins containing 6 to 60 carbon atoms, and during which the undesired dimerization and oligomerization are avoided as much as possible Such a desired industrial process for the preparation of relatively narrow band predetermined fractions of olefins, containing 18-24 carbon atoms, is mainly consisting of at least a double bond isomerization reaction and a disproportionation reaction.

Therefore there is still a need for an improved industrial disproportionation process. It is an object of the present invention to provide such a desired improved catalyst system for disproportionation of more particularly higher olefins.

SUMMARY OF THE INVENTION

This invention relates to a catalyst system for olefin disproportionation containing molybdenum oxide supported on alumina which comprises comulling a gamma-alumina providing agent with a sulfur-containing compound and/or a phosphorous containing compound and, optionally, molybdenum oxide(s) or molybdenum oxide(s) providing agents, to a homogeneous extrudable mass, extruding the mass and dividing it into small particles, drying, calcining at a temperature in the range of from 400° C. to 800° C., impregnating the obtained particles with a solution of a molybdenum oxide(s) providing agent, and optionally with a solution of a sulfur-containing compound and optionally with a solution of a phosphorous-containing compound, drying the particles and calcining the particles at a temperature in the range of from about 400°–800° C. for at least 1 hour, optionally followed by an additional impregnating step as mentioned hereinbefore whereby the final total content of molybdenum is in the range of from about 5% by weight to about 13% by weight, the final content of sulfur-containing compound is up to about 10% by weight and the final content of the phosphorous-containing compound is up to about 10% by weight, calculated on the weight of the total final composition.

DESCRIPTION OF THE PREFERRED EMBODIMENTS

The term "gamma alumina providing agent", as used herein, means any alumina starting material, which can predominantly provide the gamma-alumina phase in an irreversible way at temperatures of calcination and use of the catalyst.

The alumina starting material for the catalyst system of the present invention is preferably of the pseudo-boehmite type, which may be represented by the formula $Al_2O_3 \cdot xH_2O$, wherein x is in the range of from 1.3 to 1.8 and which is transformed into gamma-alumina during the preparation of the catalyst system as much as possible. Such pseudo-boehmite type aluminas may be obtained by a variety of preparation methods known in the art.

According to a more preferred embodiment of the present catalyst system, mixtures of pseudo-boehmite type aluminas are used in order to quench possible fluctuations in composition and to reach a constant purity starting material as much as possible.

Examples of suitable alumina starting materials are commercially available Pural (Registered Trade Mark) and Versal (Registered Trade Mark) alumina powders, which are peptized with acetic acid and/or nitric acid.

Typical examples of the final catalyst systems according to the present invention, containing gamma alumina as main ingredient, have a surface area $\geq 150$ m$^2$/g, a narrow pore size distribution, an average pore diameter in the range of from about 6 nm to about 20 nm and a water pore volume in the range of from about 0.40–0.80 ml/g.

The indicated surface areas of the gamma-alumina are all measured by the nitrogen adsorption method according to ASTM D 3663. The water pore volume and the pore diameters (by means of mercury porosimetry) have been determined as specified hereinafter.

As used herein, the term "molybdenum oxide(s) providing agent" means any molybdenum compound which provides molybdenum oxide(s) in the final catalyst composition under the conditions of the final calcination and/or the use of the catalyst system for disproportionation.

In addition to MoO₃ itself, a variety of molybdenum compounds may be used, such as molybdenum carbonyl derivatives, molybdenum oxalate, molybdenum acetate, molybdenum bicarbonate, molybdenum formate, ammonium dimolybdate, ammonium paramolybdate (ammonium hepta molybdate), molybdenum sulfide, molybdenum acetyl acetonate.

It will be appreciated that molybdenum halides will not be suitable for application in the present process, due to their corroding properties.

The molybdenum compounds to be applied may be used for comulling with starting pseudo-boehmite(s) or for the impregnation of the gamma-alumina containing products by means of a solution in an organic solvent or aqueous solution.

Preferably, ammonium dimolybdate is used, dissolved in diluted ammonia, optionally mixed with nitrilo triacetic acid (NTA) as complexing agent in the impregnating solution. The molybdenum oxide(s) content in the final catalyst composition calculated as to the weight thereof and expressed as molybdenum per se, will preferably be in the range of from 6–10% by weight.

As used herein, the term "phosphorous-containing compound" means acids of phosphorous such as phosphoric acids, phosphorous acids, phosphonic acids and their salts, or mixtures thereof Phosphates, which may suitably be used for the preparation of the catalyst system of the present invention can be selected from e.g. di(ammonium)hydrophosphate, tri(ammonium)phosphate, ammonium(dihydro)phosphate, aluminum phosphate, di(sodium)hydrophosphate, di(potassium)hydrophosphate and magnesium phosphate. In addition, phosphorpentoxide or ortho phosphoric acid can be used. Mixtures of these compounds can also be used.

As used herein, the term "sulfur-containing compound" means acids of sulfur and their salts, or mixtures thereof.

Sulfates which may suitably be used for the preparation of the catalyst system of the present invention may be selected from e.g. ammoniumsulfate, potassium sulfate and sodium hydrosulfate or mixtures thereof. Sulfuric acid and mixtures thereof may be also used.

The use of di(ammonium)hydrophosphate and/or ammoniumsulfate is preferred.

The amounts of sulfate and/or phosphate are normally in the range of from about 0.1–10% by weight, calculated on the weight of the total final catalyst composition, and more preferably in the range of from about 0.5–6% by weight.

The catalyst systems of the present invention may be prepared by methods, in principle known per se in the art. Preferably, the catalyst composition is obtained by co-mulling the starting alumina with aqueous or organic solvent solutions of the respective ingredients, to form a plastical mass, which is extruded to a particulate mass followed by drying and calcination, whereafter the obtained particles are impregnated with a solution of an (additional) molybdenum oxide(s) providing agent and optionally one or more of sulfur-containing and/or phosphorus-containing ingredients, followed by drying and calcination.

It will be appreciated that the complete impregnation, drying and calcination step may be carried out in one or more steps and that, for example, in a first step molybdenum oxide(s) or molybdenum oxide(s) providing agent(s) may be incorporated while in a second step the sulfur-containing compound and/or phosphorous-containing compound is incorporated or vice versa.

Preferably, the impregnation and subsequent drying and calcination of all ingredients will be carried out in a single step.

It will be appreciated that the finished catalyst can be in the form of extrudates (e.g. cylindrical, trilobed, quadrulobed and hollow extrudates) as well as in the form of other shapes such as agglomerates, pellets, spheres, beads and will be depending upon the type of contacting technique which utilizes the catalyst.

The first calcination step after comulling and shaping is preferably carried out at a temperature in the range of from 500° C. to 750° C.

A period in the range from 1 to 20 hours and more preferably of from 2–10 hours is applied for this first calcination. Calcination of the finished catalyst composition is preferably carried out at temperatures between 450° C. and 750° C. For this calcination, a period of at least one hour and preferably a period in the range of from 2 to 10 hours is used.

The pore diameters of the catalysts of the present invention were measured by mercury porosimetry in the following way:

A calibrated penetrometer, containing a weighed amount of sample, whose interior pores have been completely freed from moisture by heating at elevated temperature, is evacuated and subsequently filled with mercury. Under increasing hydrostatic pressure, mercury is forced into the open pores of the sample. The volume of mercury intruded into the pores by an applied intrusion pressure is calculated from the measured change of the level of mercury in the capillary of the penetrometer and the diameter of the capillary. The pore diameter is derived from the measured intrusion pressure, surface tension of mercury and contact angle between mercury and the sample using the Washburn equation for cylindrial pores:

$$\text{Pore diameter} = \frac{-4 \gamma \cos \theta}{P}$$

where
$Y$ = surface tension of mercury
$\theta$ = contact angle between mercury and sample
$P$ = hydrostatic intrusion pressure The pore diameter distribution can be defined from either the cumulative of volume changes or from incremental volume changes with decreasing pore diameter. It will be appreciated that:

(a) The intrusion volume at any value of applied pressure gives the volume of all pores having a diameter equal to or greater than the calculated diameter.

(b) Taking $\theta = 141.30$ deg., and $\Gamma = 0.4805$ Nm$^{-1}$. The Washburn equation becomes Pore diameter (d) = K1/p where, if we assume d is expressed in nm, the constant K1 takes the values:
$1.471 \times 10^6$ if P is in kPa
$1.451 \times 10^4$ if P is in atm
$1.500 \times 10^4$ if P is in dg/cm$^2$ The maximal pressure P=60.000 psi (pores down to 4 nm).

The water pore volume of the catalysts was determined according to the methods, described in principle in "Introduction to Characterization and Testing of Catalysts", J.R. Anderson and K.C. Pratt, Academic Press Australia, 1985 and adapted in the following way:

As the water pore volume depends on the moisture content of the sample, this has to be previously calcined. Thereto, the sample is heated in one hour to 500° C. and kept one hour at this temperature.

Subsequently, the sample is cooled down for one hour in an desiccator, whereafter the actual measurement is carried out as soon as possible. 25 g of the calcined catalyst is weighed out to a precision of 1 mg and transferred into a dry wide-mouthed flask of 100 ml. From a burette, an amount of water is added to the sample, corresponding with 90% of the expected pore volume and the flask is accurately stoppered.

The flask is agitated for 20 seconds and is allowed to cool down, if necessary, by placing it in a waterbath at ambient temperature for 10 minutes. The flask is dried and is shaken for 5 seconds.

0.2 ml portions of water are added stepwise. After every addition, the flask is shaken vigorously, 10 times vigorously tapped on a hard underground and immediately thereafter turned upside down carefully. If the material is no longer free flowing but is sticking to the flask wall in such a way that the bottom remains almost completely covered for two seconds or longer, the endpoint is reached. If the result is doubtful, the shaking and vigorously tapping is repeated. The time period for the determination has to be about 15 minutes. When the determination requires a shorter period, the endpoint has to be checked at 15 minutes after the start of the titration.

If the end point is then not reached, the stepwise addition of water, shaking and tapping the flask and turning upside down the flask is repeated and checking is repeated after 15 minutes again. This procedure is continued until the endpoint is reached. The water pore volume of the dried material is calculated by the equation: PV $H_2O$ (ml/g)=V/W wherein V=volume of the added water in ml and W=weight of the sample in g.

It will be appreciated that suitable catalyst systems embraced by the scope of the present invention may also be obtained by impregnating a semi-manufactured particulate product already containing the sulfate and/or phosphate or a part of the desired final amounts thereof and, optionally, a part of the desired final molybdenum amounts, with a molybdenum oxide providing agent to obtain a catalyst system with the desired final molybdenum amount and calcining the impregnated product under the hereinbefore indicated conditions.

According to a most preferred embodiment of the present invention, the catalyst is prepared by impregnation of a γ-alumina carrier, which contains 3–6% by weight molybdenum and 2% by weight phosphate previously introduced by comulling, with 3–6% by weight molybdenum, calculated as $MoO_3$.

Before the actual use of the catalyst for the disproportionation process, it is activated according to a preferred embodiment at a temperature in the range of from 400°–800° C. and more preferably at a temperature in the range of from 550°–725° C. under nitrogen for 5-20 hours.

The catalyst systems of the present invention show a significantly improved activity and selectivity as to disproportionation, reaching at least 95% as to linear olefins, whereas the dimerization and oligomerization reactions appear to be significantly reduced as compared to prior art catalysts.

The catalyst systems have shown more particularly to be suitable for disproportionation of the relatively higher olefins containing 6–60 carbon atoms.

The disproportionation may be carried out either batchwise or continuously using a fixed catalyst bed or a fluidized catalyst bed or any other mobile catalyst contacting process. Preferred reaction conditions of the disproportionation process e.g. temperature, pressure flow rates etc. may vary somewhat depending upon the specific catalyst composition, the particular feed olefin, desired products etc. The process is carried out at temperatures in the range of from 75° C. to 250° C. and under a pressure in the range of from 1 bar to 50 bar. More preferably a temperature in the range of from 100° to 150° C. is utilized.

Although the olefin reactions according to this invention are rather independent of the pressure, for most economical operation considering combination with other steps of a complete plant operation including for example, product separation and recovery, a pressure range of from 5 to 25 bars can be used conveniently.

It will be appreciated that the catalysts of the present invention show the advantage, that due to their improved stability, process economics are improved because less regenerations and change out of the catalyst are required than in processes carried out under industrial conventional operation conditions. Moreover due to a better selectivity reduced cycle stream are necessary, which also improves the process economy.

The invention is further illustrated by the following examples, however, without restricting its scope to these embodiments.

PREPARATION OF $MoO_3/Al_2O_3$ CATALYSTS

Example 1

1036 g of a commercial alumina (HDS-base, Ketjen, Registered Trade Mark), containing 2% by weight sulfate, based on the weight of the calcined composition, was mixed in a Lancaster kneader with 434 g water and 300 g acetic acid (5% by weight). After kneading for 45 minutes, a mix is obtained which is extruded subsequently in a Bonnot single screw extruder and the obtained extrudate was dried at 120° C. for 2 hours and subsequently calcined for 2 hours at 560° C.

80 g of this particulate product, mainly consisting of gamma-alumina and showing a water pore volume of 0.59 ml/g was dried at 450° C. for 1 hour and impregnated with a solution, derived from 28.7 g ammonia (25.5% by weight) and 12.89 g ammonium dimolybdate in about 10 ml of demineralized water, whereafter the total volume was adjusted to 47 ml with demineralized water, by mixing the mass in a rolling flask for 1 hour.

Thereafter, the obtained mass was dried with an airblower for 5 hours at a maximal temperature of 63° C.

Subsequently, the mass was heated in an oven up to 120° C., was kept on this temperature for 2 hours and heated up to 725° C. in 2 hours, on which temperature it was kept for 1 hour.

The obtained catalyst contained an amount of molybdenum corresponding with 12% by weight $MoO_3$, based on the weight of the final catalyst system (A), having a surface area of 310 m²/g.

Example 2

In a Lancaster mix muller were mixed together 1036 g of Ketjen HDS base (Registered Trade Mark) containing 2% by weight sulphate, 18.0 g acetic acid (3%) and 38.3 g MoO₃ (Murex, Registered Trade Mark) and 52.2 g water and the mass was kneaded during 45 minutes. The obtained paste was extruded by means of a Bonnot extruder (Registered Trade Mark) with a 1.8 mm Delrin (Registered Trade Mark) mold having 54 holes.

The extruded mass was dried at 120° C. for two hours and calcined at 560° C. for 2 hours.

100 g of the calcined product, containing as main ingredient gamma-alumina, 4% by weight molybdenum (6.0% by weight of MoO₃) and 1.9% by weight of sulfate (calculated on the weight of the total calcined composition) having a water pore volume of 0.71 ml/g, was dried at 300° C. for 16 hours and impregnated with a solution, derived from 35.04 g ammonia (25.5% by weight), 20.04 g demineralized water, 8.06 g ammonium dimolybdate and addition of water up to a volume of 70.5 ml. After impregnation, the mass is equilibrated for 1 hour.

Thereafter the obtained mass was dried with an airblower for 5 hours to a temperature of 63° C. and subsequently placed in an oven and heated to 120° C. The mass was kept at this temperature for 2 hours and subsequently heated up to 725° C. over two hours and kept at this temperature for 1 hour.

The obtained catalyst contained 12.0% by weight of MoO₃, based on the weight of the final catalyst system (B), showing a surface area of 269 m²/g, a pore volume of 0.58 m/g and an average pore diameter of 8.8 nm.

Example 3

In a Lancaster mix muller were mixed together 529 g of Kaiser Versal 250 (Registered Trade Mark), 539 g of Condea Pural SB (Registered Trade Mark), 24 g acetic acid (3% by weight), 22.3 g (NH₄)₂HPO₄, 51.1 g MoO₃ and 813 g water, whereby the obtained mass was kneaded during 0.55 hour in total.

The paste was extruded through a Delrin (Registered Trade Mark) dieplate, having 54 holes having a diameter of 1.8 mm.

The extruded mass was dried at 120° C. for two hours and calcined at 560° C. for two hours.

100 g of the product so obtained, consisting of gamma-alumina as the main ingredient and containing 4% by weight Mo (6% by weight MoO₃) and 2% by weight phosphate, and having a water pore volume of 0.71 ml/g, was calcined at 450° C. for 1 hour and subsequently impregnated with a solution derived from 34.13 g ammonia (25.5% by weight), 20.06 g demineralized water and 8.04 g ammonium dimolybdate (56.4% Mo) and added water up to 71 ml.

Thereafter the obtained mass was heated in an oven in the same way as previously described in examples 1 and 2.

The catalyst obtained contained 11.99% by weight MoO₃, based on the weight of final catalyst system (C), showing a surface area of 257 m²/g, a pore volume of 0.58 cm³/g and an average pore diameter of 9.6 nm.

Example 4

In exactly the same way as described in example 3, a catalyst (F) was prepared except that the final calcination temperature was 450° C.

Example 5

The catalyst systems hereinbefore identified by A, B, C were tested as to disproportination activity after activivation at a temperature of 550° C. under air for 5 hours and subsequently under nitrogen for 15 hours in the following way.

In the test method an activated catalyst is exposed to purified and fully isomerized model test feed ($C_{12}$ olefins) in a recirculation system.

The procedure avoids any contact of the activated catalyst with oxygen during its transport from the furnace to the recirculation system.

The performance of the activated catalyst is subseqently measured by circulating the test feed (350 ml) over the catalyst (25 grammes) at the rate of 10 l/h and at 125° C. At regular intervals, samples are taken in such a way that loss of light products is avoided.

In this closed recirculation system used, loss of light products produced in the disproportionation reaction is negligible. In this way the dimer make by the catalyst at any time during the test can be determined by calculating the decrease of the number of moles in the reaction product.

The rate of disproportionation can be determined from the decrease of the concentration of the $C_{12}$ olefin test feed with progressing reaction time. The data obtained suggest that the disproportionation reaction can be described by a (pseudo) first-order reversible reaction.

This means that for the before-described screening test the following formula can be used for the disproportionation activity and dimerization activity.

$$kt = \frac{OW}{CW} \cdot \ln \frac{1}{1 - \text{fraction } C_{12} \text{ olefins converted}}$$

wherein k represents the first order disproportionation rate constant OW represents the weight of the olefin at time period t and CW represents the weight of the catalyst and $$\frac{Mo - Mt}{Mo} \times 100\%,$$

wherein
Mo represents the number of olefin moles in feed
Mt represents the number of olefin moles in product after timeperiod t, respectively.

The obtained results with the catalyst samples A, B, C and with two commercially applied catalyst compositions (D and E) have been summarized in the following table.

TABLE

| Exp. No | Catalyst | Metal oxide % w MoO₃ comulled | Metal oxide % w MoO₃ impregn | Anion % w CoO | Anion % w SO₄ | Anion % w PO₄ | Final Calcin. temp. °C. | Disprop. Rate constant 'k' kg·kg⁻¹·h⁻¹ | Dimer make % mol % |
|---|---|---|---|---|---|---|---|---|---|
| 1 | A | — | 12 | | 2 | | 725 | 52 | 4.7 |

TABLE-continued

| Exp. No | Catalyst | Metal oxide % w MoO₃ comulled | Metal oxide % w MoO₃ impregn | Anion % w CoO | Anion % w SO₄ | Anion % w PO₄ | Final Calcin. temp. °C. | Disprop. Rate constant 'k' kg·kg⁻¹·h⁻¹ | Dimer make % mol % |
|---|---|---|---|---|---|---|---|---|---|
| 2 | B | 6 | 6 | | 2 | | 725 | 55 | 4.4 |
| 3 | C | 6 | 6 | | | 2 | 725 | 46 | 3.1 |
| 4 | D | — | 12 | 4 | 2 | | ? | 30 | 5.2 |
| 5 | E | — | 15 | 4 | | | 675 | 30 | 7 |
| 6 | F | 6 | 6 | | | 2 | 450 | 41 | 4.2 |

D = industrially used dispropotionation catalyst obtained by impregnation with MoO₃ and CoO of a support as prepared in Examples 1 and 2.
E = Commercially used disproportionation catalyst as described in GB 1,117,968 (without molecular hydrogen).

Example 6

In a continuous experiment for testing the stability, the performance of catalyst B has been compared with that of catalyst D. C₁₂ olefins isomerized in situ in an isomerization reactor prior to both disproportionation reactors was used as feed.

The test reactor was operated at an operational pressure of 5-10 bar, a temperature of 126° C. and the WHSV was in the range of 2.2-3.5 kg/kg/h. At regular intervals the WHSV was increased to 10-12 kg/kg/h to determine the activity of the catalysts to be tested, and thus its deactivation rate. The obtained results with both catalysts have been depicted in FIG. 1. The disproportionation reaction is also here described, as in Example 5, by a (pseudo) first order reaction, and the results are presented by the first order disproportionation rate constant be.

$$k = WHSV^* \ln\left[\frac{1}{1-x}\right], \text{ where}$$

$$x = \frac{C_{12}(o) - C_{12}(t)}{C_{12}(o) - C_{12}(e)}$$

wherein
$C_{12}(o)$ represents C₁₂ olefins concentration in the feed,
$C_{12}(t)$ represents C₁₂ olefins concentration in the product at time=t,
$C_{12}(e)$ represents C₁₂ olefins concentration in the product at equilibrium of the disprop. reaction (i.e. at low WHSV).

What is claimed is:

1. A process for olefin disproportionation using a catalyst system comprising molybdenum oxide supported on alumina prepared by a process which comprises:
   (a) comulling a gamma alumina providing agent with a sulfur-containing compound and/or a phosphorus-containing compound to produce a homogeneous mass,
   (b) extruding the mass and dividing it into small particles,
   (c) drying and calcining said particles at a temperature in the range of from about 400° C. to about 800° C.
   (d) subjecting said particles at least once to an additional step comprising: (1) impregnating said particles with a solution of molybdenum oxide(s), (2) drying and (3) calcining said impregnated particles at a temperature in the range of from about 400° C. to about 800° C.

2. The process of claim 1 wherein in step (a), said gamma alumina providing agent is additionally co-mulled with a molybdenum oxide(s) providing agent.

3. The process of claim 1 wherein in step (a), said gamma alumina providing agent is additionally co-mulled with the molybdenum oxide(s).

4. The process of claim 1 wherein said solution in step (d) additionally contains a sulfur-containing compound.

5. The process of claim 1 wherein said solution in step (d) additionally containing a phosphorus-containing compound.

6. The process of claim 1, 2 or 3 wherein said catalyst system contains from about 5 percent by weight to about 13 percent by weight molybdenum.

7. The process of claim 1 or 4 wherein said catalyst system contains from about 0 percent by weight to about 10 percent by weight sulfur-containing compound.

8. The process of claim 1 or 5 wherein said catalyst system contains from about 0 percent by weight to about 10 percent by weight phosphorus-containing compound.

9. The process of claim 1 wherein said catalyst system has a surface area of $\geq 150$ m²/g, a narrow pore size distribution, an average pore diameter in the range of from about 6 Nm to about 20 Nm and a water pore volume in the range of from about 0.40 to about 0.80 ml/g.

10. The process of claim 1 wherein said gamma alumina providing agent is a pseudo-boehmite type alumina which is represented by the formula Al₂O₃·xH₂O, wherein x is in the range of 1.3 to 1.8.

11. The process of claim 1 wherein said gamma alumina providing agent is derived from a mixture of pseudo-boehmite type aluminas.

12. The process of claim 2 or 3 wherein said molybdenum oxide(s) is selected from the group consisting of MoO₃, a molybdenum carbonyl derivative, molybdenum acetate, molybdenum oxalate, molybdenum bicarbonate, molybdenum formate, ammonium dimolybdate, ammonium paramolybdate, molybdenum sulfide, molybdenum acetyl acetonate and mixtures thereof.

13. The process of claim 2 or 3 wherein said molybdenum oxide(s) is derived from ammonium dimolybdate.

14. The process of claim 1, 2 or 3 wherein the molybdenum oxide(s) content in the final composition, expressed as molybdenum per se, is in the range of from about 6% by weight to about 10% by weight.

15. The process of claim 1 or 5 wherein said phosphorus-containing compound is selected from di(ammonium)hydrophosphate, tri(ammonium)phosphate, ammonium(dihydro)phosphate, aluminium phosphate, di(sodium)hydrophosphate, di(potassium)hydrophosphate, magnesium phosphate and mixtures thereof.

16. The process of claim 1 or 5 wherein said phosphorus-containing compound is selected from phosphorpentoxide and phosphorus acid.

17. The process of claim 1 or 4 wherein said sulfur-containing compound is selected from ammonium sulfate, potassium sulfate, sodium hydrosulfate and mixtures thereof.

18. The process of claim 1 or 5 wherein said phosphorus-containing compound is derived from di(ammonium)hydrophosphate.

19. The process of claim 1 or 4 wherein said sulfur-containing compound is derived from ammonium sulfate.

20. The process of claim 1 or 4 wherein said catalyst system contains from about 0.5% by weight to about 6% by weight sulfur-containing compound, calculated on the weight of the total final catalyst composition.

21. The process of claim 1 or 5 wherein said catalyst system contains from about 0.5% by weight to about 6% by weight phosphorus-containing compound, calculated on the weight of the total final catalyst composition.

* * * * *